Figure 1:
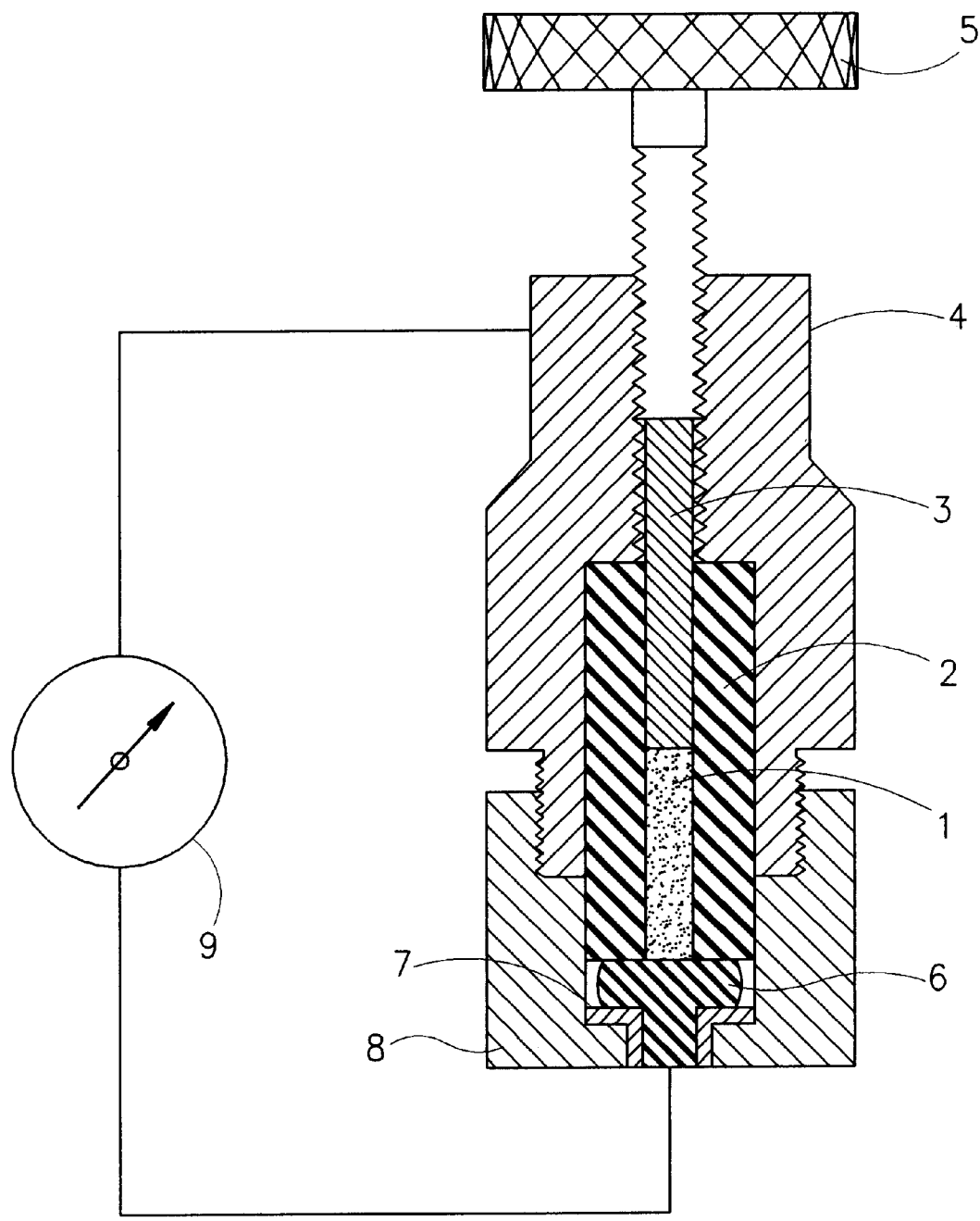

_US Patent_

United States Patent [19]
Filanovsky et al.

[11] Patent Number: 6,015,522
[45] Date of Patent: Jan. 18, 2000

[54] METHOD FOR LOW-TEMPERATURE PREPARATION OF ELECTRODES FROM CONDUCTING REFRACTORY POWDER MATERIALS

[75] Inventors: Boris Filanovsky; Tat'yana Burenko; Ilya Kuselman; David Simantov; Avinoam Shenhar, all of Jerusalem, Israel

[73] Assignee: State of Israel, Ministry of Industry & Trade, National Physical Laboratory of Israel, Jerusalem, Israel

[21] Appl. No.: 08/953,979

[22] Filed: Oct. 20, 1997

[30] Foreign Application Priority Data

Oct. 20, 1996 [IL] Israel ............................... 119448

[51] Int. Cl.[7] .................................................. C04B 35/00
[52] U.S. Cl. ........................ 264/105; 264/104; 264/317
[58] Field of Search ................................ 264/104, 105, 264/317

[56] References Cited

U.S. PATENT DOCUMENTS

| 5,141,828 | 8/1992 | Bennion et al. | 429/210 |
| 5,698,147 | 12/1997 | Chern et al. | 264/104 |

OTHER PUBLICATIONS

"Voltammetric Differentiation of Ascorbic Acid and Dopamine at an Electrochemically Treated Graphite/Epoxy Electrode", Ladislav Falat et al., Anal. Chem., vol. 54, 1982, pp. 2108–2111.

"Lanthanum Hexaboride and Titanium Nitride as Electrode Materials for Volammetry", B. K. Filanovskii et al., Plenum Publishing Corp., 1988, pp. 119–122.

"Voltammetry of Mixed Tungsten–Titanium Carbide in Nonaqueous and Mixed Solvents", B. Hofman et al., Plenum Publishing Corp., 1989, pp. 1175–1178.

"The Voltammetric Characteristics of Tungsten–Carbide–Based Electrodes in Some Nonaqueous and Mixed Solvents", B. Hofman et al., Plenum Publishing Corp., 1989, pp. 1113–1114 and 1116–1117.

"Sol–Gel Vanadium Pentaoxide Glucose Biosensor", Victor Glezer et al., J. Am. Chem. Soc., vol. 115, 1993, pp. 2533 and 2534.

"Voltammetric Studies of Composite Ceramic Carbon Working Electrodes", G. Gun et al., Analytica Chimica Acta, vol. 294, 1994, pp. 261–270.

"UV–Polymerizable Screen–Printed Enzyme Pastes", Ingrid Rohm et al., Anal. Chem., vol. 67, No. 13, Jul. 1, 1995, pp. 2304–2307.

(List continued on next page.)

_Primary Examiner_—James Derrington
_Attorney, Agent, or Firm_—Evenson, McKeown, Edwards & Lenahan PLLC

[57] ABSTRACT

A novel method for preparation of electrodes at a low temperature from electroconducting refractory powder materials. The electrodes are useful for analytical purposes. The method is based on cold pressing of the powders, wetted with solution of a polymer and placed into a disposable frame of the same polymer, with the help of a laboratory hand device producing a relatively small pressure. Control of the end of pressing is done by means of measurement of the electrode resistance. A puncheon serves as a current conductor. Electrodes thus prepared have a low resistance, a high sensitivity and stability. In comparison with glassy carbon electrodes, the most widely applied ones in electroanalytical chemistry, the novel electrodes are cheaper, yet not inferior to such glassy carbon electrodes, and even sometimes better. For example, an electrode prepared from titanium nitride powder has a wider anodic range of potentials and may be used for determination of compounds containing SH-groups, which is impossible to achieve with glassy carbon electrode.

10 Claims, 5 Drawing Sheets

OTHER PUBLICATIONS

"Enhanced Signal–to–Background Raticos in Voltammetric Measurements Made at Diamond Thin–Film Electrochemical Interfaces", Jerzy W. Strojek et al., Anal. Chem., vol. 68, 1996, pp. 2031–2037.

"Dynamic Electrochemistry: Methodology and Application", James L. Anderson et al., Anal. Chem., vol. 68, No. 12, Jun. 15, 1996, pp. 379R–444R.

"Electrochemical Methods, Fundamentals and Applications", Allen J. Bard et al., pp. 283–293, n.d.

METHOD FOR LOW-TEMPERATURE PREPARATION OF ELECTRODES FROM CONDUCTING REFRACTORY POWDER MATERIALS

FIELD OF THE INVENTION

Present invention relates to electroanalytical chemistry and in particular with methods of electrode preparation from conductive refractory powders to be uses for analytical purposes.

BACKGROUND OF THE INVENTION

Electrodes from carbon powders are used widely in electroanalytical chemistry. There is an increasing interest in electrodes prepared from sulfides, carbides, silicides, nitrides, borides and oxides of transitional metals (J. L. Anderson, E. Bowden, P. Piceep. Anal. Chem., 1996, v.68, pp. 379R–444R). These refractories are produced as conductive powders with high chemical and electrochemical stability. The main difficulty in preparation of electrodes from such powders is the high specific electrical resistance of the initial powdery material ($\rho \geq 10^6 \Omega \cdot cm$), high hardness (5–9 units on the scale, in which diamond hardness is 10 units) and high melting temperatures (2500–3000° C.).

Two main kinds of such electrodes are widely used: paste and sintered electrodes. Carbon paste electrodes are produced from mixtures of a carbon powder with an inert liquid (paraffin oil, silicone etc.) which is an electrical insulator and which is insoluble in the electrolytes used. The drawbacks of carbon paste electrodes are their relatively low stability and reproducibility (E. Gun, M. Tsionsky, O. Lev. Anal. Chem., 1994, v.66, pp. 261–270).

Solid electrodes from carbon powder with different polymers (Teflon©, epoxy resin, polyacrylamide etc.) are known (L. Falat, Ch. Y. Cheng. Anal. Chem., 1982, v.54, pp. 2108–2111). Preparing such electrodes from low conductivity powders (for example, titanium nitride) is practically impossible because of the high resistance of the electrodes ($R \geq 10^4 \Omega$). The attempt of sol-gel technology application for preparation of electrodes from low conductivity powder of $V_2O_5$ was unsuccessful due to this reason. (V. Gleser, O. Lev. J. Amer. Soc., 1993, v.115, p.2533). Similar is the use of screen-printing paste (J. Rohm, W. Kunneka et. al. Anal. Chem., 1995, v.67, pp. 2304–2307) which has the same drawback—high electrical resistance of electrodes.

B. Filanovsky, L. Nadezina et. al. (Zav. Lab., 1988, v.54, N 2, pp.13–16) used high temperature dusting of powder on a corresponding matrix for titanium nitride powder. This method does not allow to eliminate the effect of the matrix on the measurement results. Besides, this technology is complicated and expensive.

The most effective method for preparation of electrodes from powders with high electrical resistance is high temperature treatment (sintering) of previously pressed powder tablets in an inert atmosphere. B. Hofman and H. Shell (Electrokhimiya, 1988, v. 24, pp.1199–1203 and 1264–1267) prepared electrodes from titanium carbides $Ti_xC_y$ and titanium nitrides $Ti_xN_y$, where $0,7<x<1,5$ and $0.7<y<1.5$, at the temperature ~2000° in hydrogen atmosphere. This is a precursor of our invention. The drawback of the known method is the dependence of electrochemical properties of the electrodes produced on the preparation conditions (temperature, pressure and composition of atmosphere) which influence the stoichiometry and porosity of the product.

Evaluation of the novel electrodes in analytical methods is usually conducted by comparison with the most widely used glassy carbon electrodes (see, for example, J. W. Strojek, M. Grander, G. Swan. Anal. Chem., 1996, v.68, pp. 2031–2037).

SUMMARY OF THE INVENTION

An aim of this invention is the development of a simple, inexpensive and convenient method for low-temperature preparation of electrochemical electrodes from non-conducting refractory powders at room temperature.

The novel method is based on the pressing of the powders in a collapsible device, which is shown on FIG. 1, where 1—material of electrode, 2—disposable plastic frame, 3—metallic puncheon-contact, 4—metallic nozzle, 5—metallic screw for pressure application, 6—metallic bush-contact, 7—insulating plastic washer, 8—metallic matrix, 9—ohmmeter. This device permits to produce electrodes both from carbon powders with high conductivity, and from badly conducting powders (titanium nitride etc.).

Powder 1 is wetted with a solution of the polymer from which the disposable frame 2 is made. Wetted powder is placed into the frame and filled to ⅓–¼ of its volume. Pressing is conducted at room temperature by rotating screw 5. Effort of the pressing is transmitted by puncheon 3, and the process of the pressing is controlled by measuring the electrical conductivity of the sample with ohmmeter 9. For this purpose one contact of the ohmmeter is connected to nozzle 4, and the other one—with bush 6 insulated from matrix 8 by nozzle 7. After reaching the necessary value of resistance ($R<50\Omega$) the pressure is maintained during 30–60 min for the hardening of the electrode. During this time a part of the solvent reaches the walls of the electrode frame, dissolves them partly and forms a protecting layer. The layer prevents electrolyte leakage while using the electrode and so excludes its edge effects.

After hardening of the material the device is disconnected and the prepared electrode is extracted from it. Puncheon 3 is left in the electrode and serves as electrical contact.

To prepare the surface of the electrode from a carbon powder for use it is cleaned with abrasive paper, and then it is polished with $Al_2O_3$ powder. To prepare the surface of an electrode produced from a hard powder (titanium nitride etc.) it is polished with the same powder wetted with the solution of the same polymer that was used at the beginning of the whole procedure, but diluted with the solvent in a ratio 1:3–1:4. The polishing is finished with dry powder.

The novel method, as distinguished from the precursor (B. Hoffman, H. Shell, Electrokhimiya, 1988, v. 24, pp.1199–1203 and 1264–1267), allows the following:

1. To obtain electrodes without thermal and/or chemical influence on the used material and, thus, without changing its stoichiometry;
2. To use a cheap disposable frame and other details of the electrode from commercially available materials that eliminate the problem of electrode contamination during its application (memory effect);
3. To control the end of the process of electrode preparation according to its electrical resistance;
4. To insert different modifying compounds into the electrode volume (promoting the electrode) so as to expand essentially the electrodes application field.

EXAMPLES

Example 1

As materials for the device, steel (items 4–6 and 8 in FIG. 1) and Teflon (item 7 in FIG. 1) were used. Puncheon (detail 3 in FIG. 1) was made also from steel, and frame 2 of the electrode—from polymethylmetacrylate.

As a powder with low electrical resistance and low hardness, fine graphite powder was used (Merck, more than 99.5% of particles of sizes ≦50 μm).

As polymer solution, 3% polymethylmetacrylate (Aldrich, average molecular weight ~120000) in dichloroethane was used. The "solution-powder" mixture was prepared in the ratio 0.04 ml of solution to 200 mg of the powder. The electrode frame was prepared from the same polymer. The channel of the electrode frame (Ø 2 mm) was filled up to ~¼ of its height (~12 mm), the device was assembled and pressure was applied by screw 5. After achieving the pressure value when the resistance of the material was equal to 10Ω ($\rho$=0.3Ω·cm), the pressure was maintained for ~1 hour and then the device was disconnected.

Preparation of the electrode working surface for the use was performed by cleaning and then polishing with $Al_2O_3$ (sizes of particles–0.3 μm).

The results of the tests of this electrode and electrodes of Examples 2–4: see below.

Example 2

As powder with high electrical resistance and high hardness, TiN was used (Aldrich, more than 99% of particles have sizes ≦10 μm). All other conditions of the electrode preparation were the same as in Example 1. Preparation of the working surface was done by cleaning and then polishing with powdery TiN wetted by a solution of 1% polymethylmetacrylate in dichloroethane, and then with the dry powder of TiN.

Example 3

As powder with high electrical resistance and high hardness TaN was used (Aldrich, more than 99.5% of particles have sizes ≦5 μm.) All other conditions of electrode preparation were the same as in the previous Examples. Polishing was done with powdery TaN (by analogy with Example 2).

Example 4

As powder with high electric resistance and high hardness, NbN was used (Aldrich, sizes of particles are ≦44 μm). Pressing of the material was completed at a resistance of 40Ω($\rho$=1.3Ω·cm). All other conditions were the same as in Examples 1–3. Polishing was performed with NbN powder (by analogy with Examples 2 and 3).

TESTING OF THE NOVEL ELECTRODES

The novel electrodes were tested by comparison with glassy carbon electrodes (GCE).

Comparison was conducted in the mode of a stationary electrode (SE) and a rotating disk electrode (RDE). Voltammetric measurements were performed with a potentiostat PAR M263A and Software 270/250 (EG&G Instruments, USA), and with Polarecord E 506 (Metrohm, Switzerland). Auxiliary electrode—Pt wire Ø 0.5 mm, and reference electrode—Ag/AgCl/KCl sat. were used in all measurements. A salt bridge (Metrohm, Switzerland) and a 3-electrode cell were filled with the same solutions.

Evaluation of the effective surface of the electrodes. A novel electrode Ø2 mm produced by the novel method from carbon powder described above, named "C-press electrode" was compared with GCE (Metrohm, Ø 2 mm).

Figure 2:
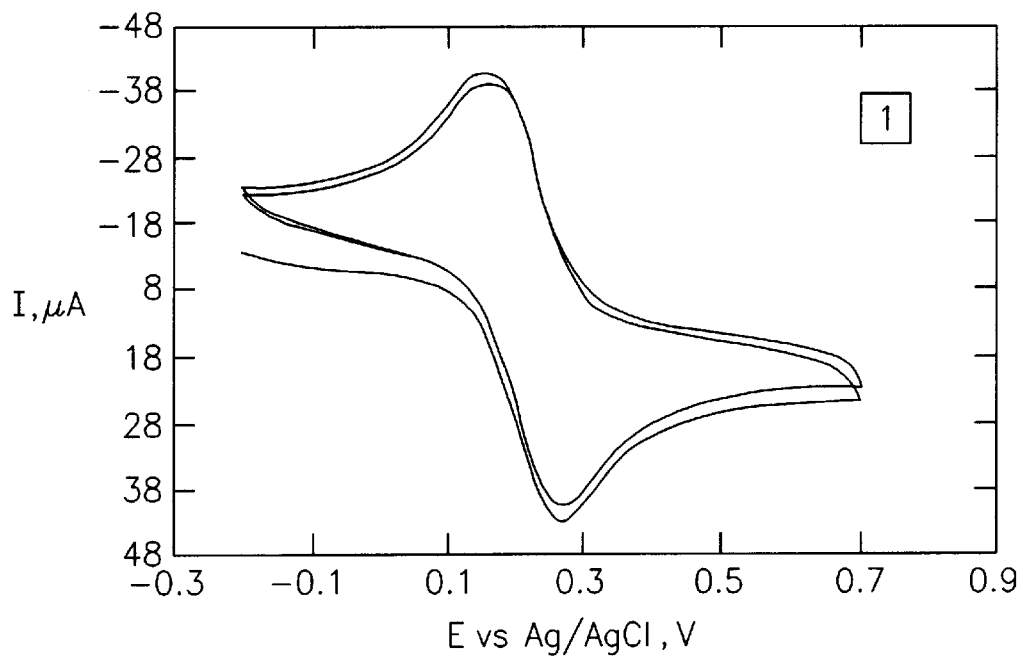
Figure 2:
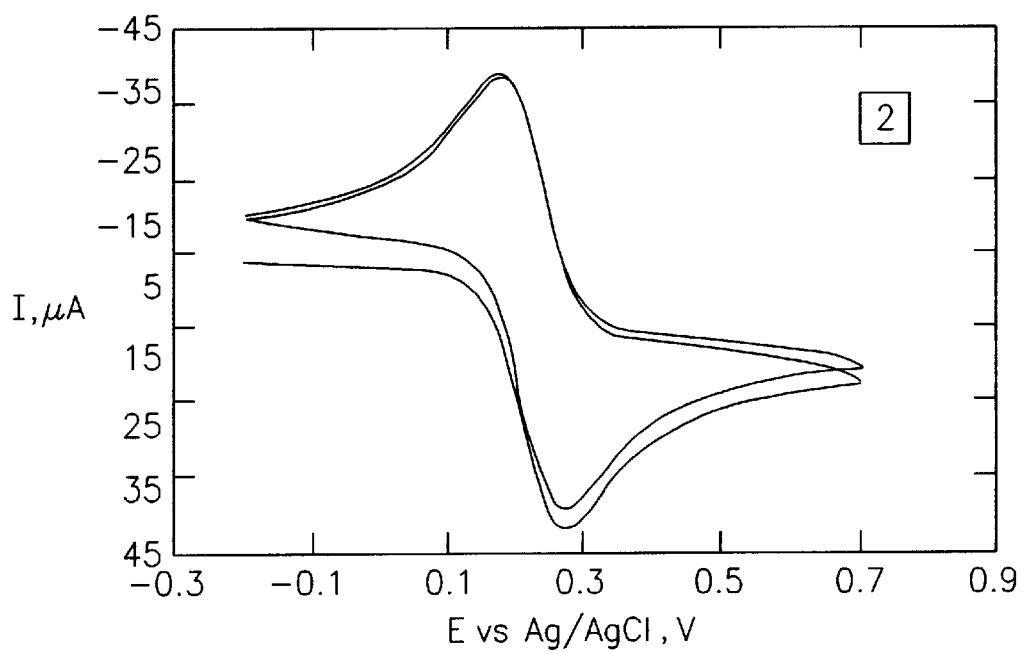

Cyclic voltammograms for both types of electrodes in 2 mM solution of ferri-ferrocianide with 0.2 M HCl as a reference solution are shown in FIG. 2. Their comparison demonstrates that the surface of the novel electrode is not contaminated by traces of reagents or materials used during its preparation.

Figure 3:
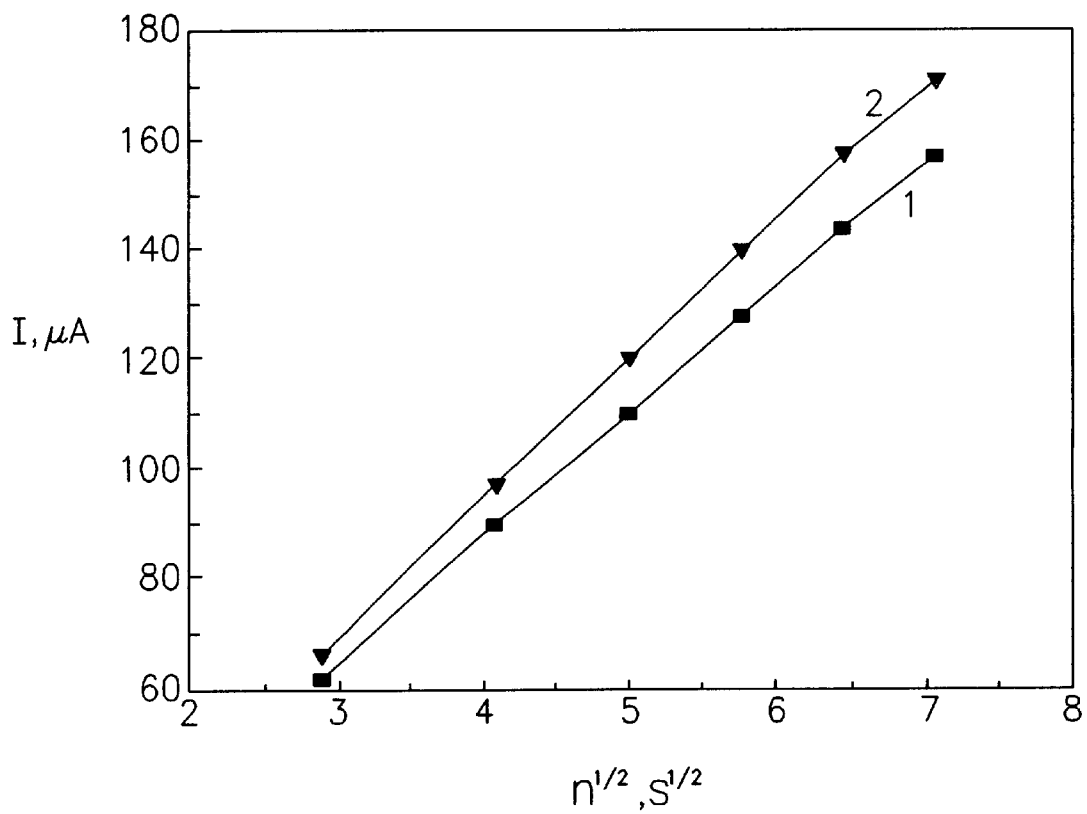

Dependence of maximum current I at potential E=−0.2 V (minus background current $I_0$) on the number n of RDE rotations per second in the range n≦50 r/s is shown in FIG. 3 for 1 M solution of ferrocyanide with 0.1 M KCl+0.01 M HCl as background solution. The difference in the slopes of the curves under identical conditions occurs because the surface of the novel electrode is partly occupied by polymethylmetacrylate. Using Levitch equation (see, A. Bard, L. Faulkner. Electrochem Methods, 1980, J. Wiley, p.283) one can calculate from the ratio of the slopes (FIG. 3) that the working surface of the C-press electrode corresponds to 90.2% of the GCE surface. Remaining 9.8% is the part of the surface of the C-press electrode occupied by polymethylmetacrylate.

Figure 4:
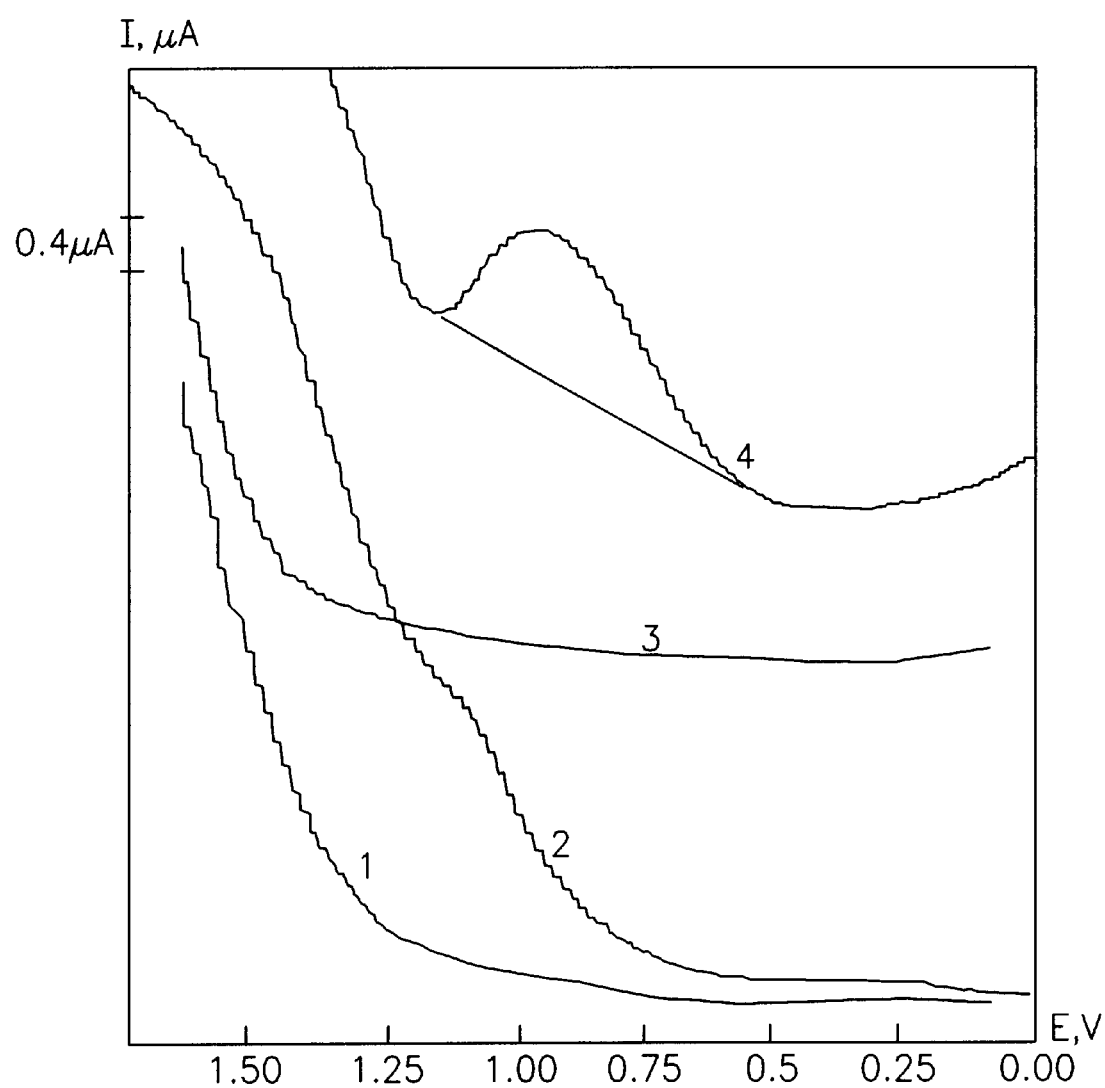

Comparison of ranges of potentials (windows). Comparison was performed for potentials from $E_{H2\uparrow}$ to $E_{O2\uparrow}$ for GCE and novel electrodes from carbon (C-press), titanium nitride (TiN-press), tantalum nitride (TaN-press), and niobium nitride (NbN-press). The ranges were evaluated by cyclic voltammetry method for stationary electrode in solutions of 0.1 M $HNO_3$, 0.1 M $KNO_3$, and 0.05 M $Na_2B_2O_7$ (pH=9.18) prepared from Merck reagents. Results of the evaluation are shown in Table 1. From these data one can see that novel electrodes have higher values of the potential $E_{O2\uparrow}$ in comparison with GCE, i.e. their range of potentials is shifted to the anodic direction. This displacement ($E_{O2\uparrow press} - E_{O2\uparrow GCE}$) in acid and neutral solutions is for TiN 200–300 mV for TaN 300–400 mV for NbN −500 mV. In basic solutions this displacement is 100 mV for TiN, 300 mV for TaN and 300 mV for NbN. This fact indicates advantages of the novel electrodes in the anodic range, in particular, at determination of substances having SH-group. For example, FIG. 4 illustrates AC voltammograms I(E) for GCE and TiN-press electrodes in the presence of 1 mM α-monothioglycerol (α-MTG) using as background 0.1 M KCl+0.01 M HCl, stationary electrode, first harmonic, amplitude of alternating current −25 mV, frequency −75 Hz. From FIG. 4 it follows that GCE does not practically produce a useful signal, while in the curve of TiN-press electrode the peak of monothioglycerol is expressed clearly at E=+0.97÷0.98 V. This signal increases, if the rotating electrode is used. Thus, under the same conditions, E=+0.97÷0.98 V and rate of rotating 1000 r/min, the following dependence of maximum current (I) from concentration of α-MTG ($C_{\alpha-MTG}$) was obtained:

$$I=0.66+1.90\, C_{\alpha-MTG},$$

where the range of concentrations $C_{\alpha-MTG}$ is 0.1–1.0 mM, corresponding range of currents I is 0.8–2.5 μA, standard deviation of the slope equals 0.10 μA/mM, residual standard deviation −0.07 μA, square of the correlation coefficient −0.99, and a number of degrees of freedom −4.

Evaluation of the Homogeneity of the Electrodes

Figure 5:
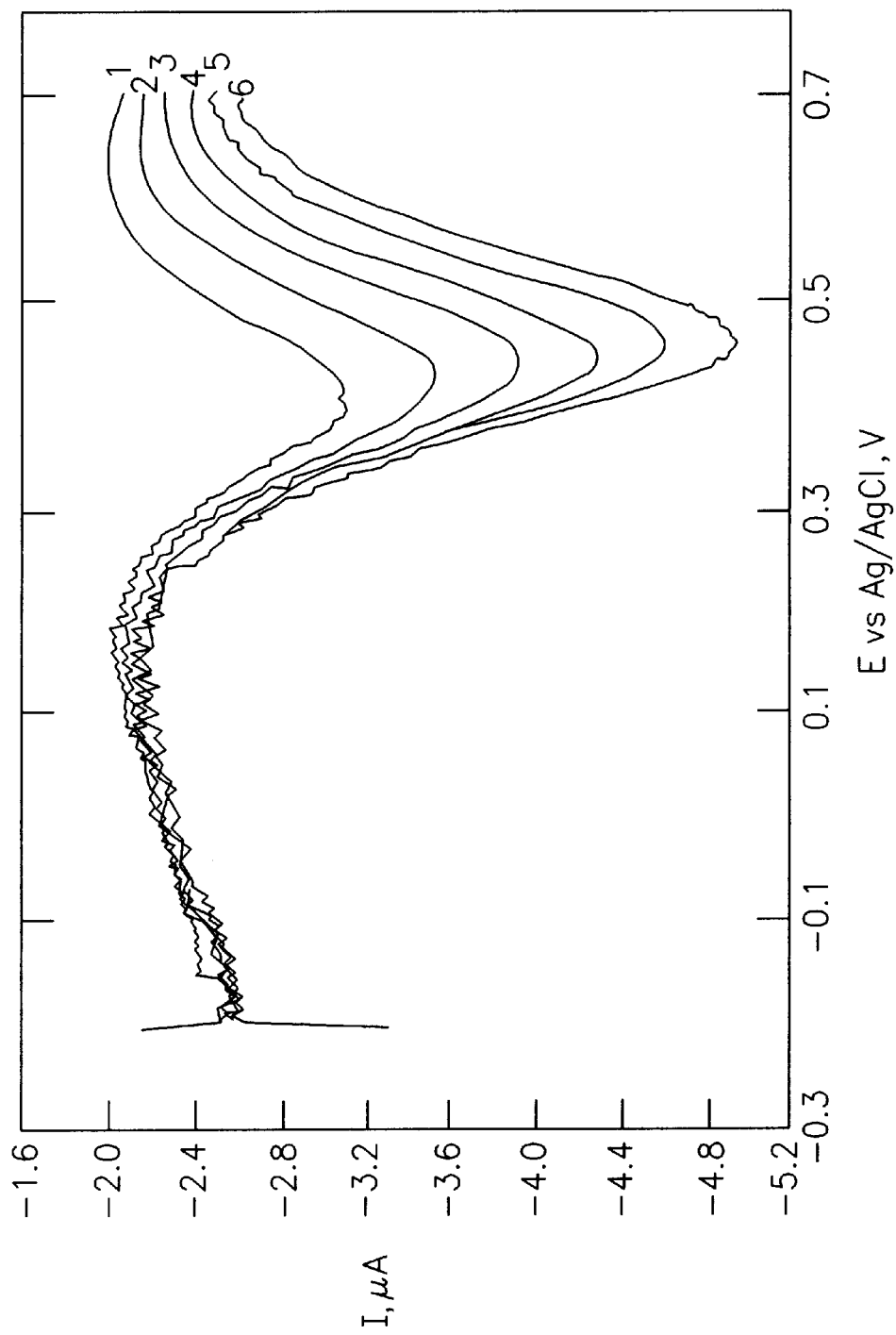

Evaluation of homogeneity of the new electrodes was done by comparison of calibration curves for dependence of I on ferrocyanide concentration ($C_{Fe}$=0.2–1.2 mM) in solution 0.1 M KCl+0.01 M HCl for three samples of TiN-press electrodes made under the same conditions. These curves (each by 6 points, i.e. 6 values of $C_{Fe}$) were obtained for each example in five replicates. Before each replicate the working surface of an electrode was renewed by cleaning and polishing. In such a manner 3×5=15 working surfaces were prepared and I was measured 15×6=90 times. For example, corresponding raw data from one of the surfaces are shown in FIG. 5. From such data the linear regression equations I ($C_{Fe}$) describing the calibration curves were calculated by the least square method. Regression coefficients (intercept a and slope b), standard deviation of slope $S_b$, residual standard deviation $S_R$, and square of correlation coefficient $r^2$ at 6−2=4 degrees of freedom are shown in Table 2. The variance of averages for a sample values of the slope (between samples variance) is 1.63 with 3−1=2 degrees of freedom. The average variance of the slope values for each sample separately (intra-samples variance) is 0.73 with (5−1)×3=12 degrees of freedom. By Fisher criterion at level of confidence 0.95 and appointed degrees of freedom (2 and 12) we have:

$$F = 1.63/0.73 = 2.22 < F_{0.95}(2; 12) = 3.88$$

From this comparison it follows that the difference between slope values for samples of the electrode does not exceed corresponding difference for working surfaces in a separate sample, i.e. that new electrodes are homogeneous.

Note, the variances may be decreased by limitation of the difference in the sizes of the powder particles, improving of the electrode material mixing, optimization of the conditions of polishing and so on.

TABLE 1

POTENTIAL RANGES FOR NOVEL ELECTRODES IN DIFFERENT MEDIA

| Electrode | C-press | TiN-press | TaN-press | Nb-press | GCE |
|---|---|---|---|---|---|
| Media | | | 0.1 M $HNO_3$ | | |
| $E_{O2\uparrow}$, V | +1.4 | +1.6 | +1.7 | +1.8 | +1.3 |
| $E_{H2\uparrow}$, V | −1.0 | −0.55 | −0.7 | −0.6 | −1.0 |
| Media | | | 0.1 M $KNO_3$ | | |
| $E_{O2\uparrow}$, V | +1.35 | +1.2 | +1.4 | +1.6 | +1.1 |
| $E_{H2\uparrow}$, V | −0.9 | −0.8 | −1.15 | −1.0 | −1.1 |
| Media | | | 0.05 M $Na_2B_4O_7$ | | |
| $E_{O2\uparrow}$, V | +1.1 | +1.3 | +1.4 | +1.4 | +1.0 |
| $E_{H2\uparrow}$, V | −1.3 | −1.0 | −1.3 | −1.2 | −1.35 |

TABLE 2

DEPENDENCE I ($C_{Fe}$) FOR TiN - PRESS ELECTRODES IN THE RANGE OF FERROCIANIDE CONCENTRATIONS $C_{Fe}$ = 0.2−1.2 mM

| Electrode sample, No. | Calibrat curve, No. | Intercept a, μA | Slope b, μA/mM | STD of slope, $S_b$ μA/mM | Residual STD $S_R$, μA | Square of corr. coeff., $r^2$ |
|---|---|---|---|---|---|---|
| 1 | 1 | 0.34 | 1.87 | 0.04 | 0.03 | 1.00 |
|   | 2 | 0.15 | 3.28 | 0.12 | 0.10 | 0.99 |
|   | 3 | 0.28 | 4.03 | 0.04 | 0.03 | 1.00 |
|   | 4 | 0.09 | 2.93 | 0.08 | 0.07 | 1.00 |
|   | 5 | 0.26 | 4.32 | 0.11 | 0.10 | 1.00 |
| 2 | 1 | 0.69 | 2.40 | 0.25 | 0.21 | 0.96 |
|   | 2 | 0.34 | 2.08 | 0.22 | 0.18 | 0.96 |
|   | 3 | 0.55 | 2.85 | 0.17 | 0.14 | 0.99 |
|   | 4 | 0.50 | 2.20 | 0.14 | 0.12 | 0.98 |
|   | 5 | 0.36 | 2.54 | 0.14 | 0.11 | 0.99 |
| 3 | 1 | 0.42 | 3.20 | 0.12 | 0.10 | 0.99 |
|   | 2 | 0.24 | 5.45 | 0.38 | 0.32 | 0.98 |
|   | 3 | −0.20 | 5.98 | 0.17 | 0.15 | 1.00 |
|   | 4 | −0.32 | 6.48 | 0.20 | 0.16 | 1.00 |
|   | 5 | −0.05 | 6.15 | 0.23 | 0.20 | 0.99 |

FIG. 1. Device for preparation of electrodes from conducting powders. 1—material of electrode, 2—electrode frame, 3—puncheon-contact, 4—nozzle, 5—screw, 6—bush-contact, 7—insulating washer, 8—matrix, and 9—ohmmeter.

FIG. 2. Cyclic voltammograms in ferri-ferrocianide solutions. 1—C-press electrode, 2—GCE.

FIG. 3. Dependence I vs n for RDE. 1—C-press electrode, 2—GCE.

FIG. 4. Dependence I vs E. 1—GCE in 0.1 M KC1+0.01 M HC1, 2—GCE in 1 mM α-monothyoglicerol, 3—TiN-press electrode in 0.1 M KCl+0.01 M HC1, 4—TiN-press electrode in 1 mM α-monothyoglicerol.

FIG. 5. Dependence I vs E for TiN-press electrode in solutions of $K_4[Fe(CN)_6]$ in 0.1 M KCl+0.01 M HC1: 1—0.2 mM $K_4[Fe(CN)_6]$, 2—0.4 mM, 3—0.6 mM, 4—0.8 mM, 5—1.0 mM, and 6—1.2 mM.

We claim:

1. A method for low-temperature preparation of electrochemical electrodes from electroconducting refractory powders which comprises:
   mixing a refractory powder with an effective amount of solution of a polymer to prepare a mixture,
   pressing this mixture in a disposable polymer frame with a metal puncheon in a collapsible device,
   hardening the mixture under pressure to form an electrode, and
   cleaning and polishing the working surface of the electrode.

2. A method according to claim 1 where carbon powder with low electrical resistance and low hardness is used.

3. A method according to claim 1 where nitride powder with high electrical resistance and high hardness is used.

4. A method according to claim 1 where the disposable polymer frame is prepared from polymethylmethacrylate.

5. A method according to claim 1 where the solution of the polymer comprises 3–6% by weight of polymethylmethacrylate in dichlorethane employed in 0.1–0.3 g of the solution of polymer to 1 g of the refractory powder.

6. A method according to claim 1 where the metal puncheon is prepared from steel and is left in the electrode to serve as an electrical contact of the electrode.

7. A method according to claim 1 where, after pressing, the mixture is conserved under pressure for 0.5–1.0 hour for hardening and formation of a protecting layer between the frame and the electrode material.

8. A method according to claim 1, further comprising polishing the working surface of the electrode with aluminum oxide.

9. A method according to claim 3, further comprising polishing the working surface of the electrode with the refractory powder used for the electrode preparation.

10. A method according to claim 3, wherein said powder is a nitride of titanium.

* * * * *